(12) United States Patent
Ihde

(10) Patent No.: US 7,909,605 B2
(45) Date of Patent: Mar. 22, 2011

(54) SCREW IMPLANT APPARATUS AND METHOD

(75) Inventor: Stefan Ihde, Uetliburg (CH)

(73) Assignee: Biomed Est. (LI)

( * ) Notice: Subject to any disclaimer, the term of this patent is extended or adjusted under 35 U.S.C. 154(b) by 469 days.

(21) Appl. No.: 11/788,985

(22) Filed: Apr. 23, 2007

(65) Prior Publication Data

US 2007/0287129 A1 Dec. 13, 2007

(51) Int. Cl.
*A61C 8/00* (2006.01)

(52) U.S. Cl. .......................................... 433/174

(58) Field of Classification Search .......... 433/172–176, 433/201.1, 202.1, 215, 220, 221; 427/2.26, 427/2.29; 606/306, 301, 305
See application file for complete search history.

(56) References Cited

U.S. PATENT DOCUMENTS

| | | | | |
|---|---|---|---|---|
| 4,050,157 A | * | 9/1977 | Fagan et al. | 433/176 |
| 4,146,936 A | * | 4/1979 | Aoyagi et al. | 433/176 |
| 4,379,694 A | * | 4/1983 | Riess | 433/201.1 |
| 4,645,435 A | | 2/1987 | Sugimoto | |
| 4,758,161 A | * | 7/1988 | Niznick | 433/173 |
| 4,990,161 A | * | 2/1991 | Kampner | 623/18.11 |
| 5,527,183 A | | 6/1996 | O'Brien | 433/174 |
| 5,674,844 A | * | 10/1997 | Kuberasampath et al. | 514/12 |
| 5,837,275 A | * | 11/1998 | Burrell et al. | 424/409 |
| 5,998,390 A | * | 12/1999 | Ramamurthy et al. | 514/94 |
| 6,017,885 A | * | 1/2000 | Bagi et al. | 514/12 |
| 6,399,592 B1 | * | 6/2002 | Whiteford | 514/109 |
| 6,478,822 B1 | * | 11/2002 | Leroux et al. | 623/17.14 |
| 6,702,855 B1 | * | 3/2004 | Steinemann et al. | 623/23.53 |
| 2004/0137406 A1 | * | 7/2004 | Kennard | 433/174 |
| 2004/0235728 A1 | * | 11/2004 | Stoch et al. | 514/12 |
| 2005/0079201 A1 | * | 4/2005 | Rathenow et al. | 424/424 |
| 2005/0148512 A1 | * | 7/2005 | Hunter et al. | 514/12 |
| 2006/0046229 A1 | * | 3/2006 | Teich | 433/173 |
| 2006/0121415 A1 | * | 6/2006 | Anitua Aldecoa | 433/165 |
| 2006/0216673 A1 | * | 9/2006 | Park | 433/173 |

FOREIGN PATENT DOCUMENTS

| | | |
|---|---|---|
| DE | 41 27 839 A1 | 1/1990 |
| DE | 39 18 309 A1 | 6/1990 |
| DE | 196 28 464 A1 | 1/1998 |
| DE | 196 30 034 A1 | 4/1998 |
| DE | 203 06 008 U1 | 2/2003 |
| EP | 1 468 658 A1 | 10/2004 |
| WO | WO 2006/102054 * | 9/2006 |

OTHER PUBLICATIONS

Nagashima et al. Bisphosphonate delays the repair of cortical bone defect after drill-hole injury by reducing terminal differentiation of osteoblasts in the mouse femur. Bone 36 (2005) 502-511.*

* cited by examiner

*Primary Examiner* — Cris L Rodriguez
*Assistant Examiner* — Heidi M Eide
(74) *Attorney, Agent, or Firm* — Robert C. Haldiman; Husch Blackwell LLP

(57) ABSTRACT

An enossal screw implant is inserted cortically into the jawbone as an implant base and a mount for the superstructure of a tooth replacement or a substructure. A break point is provided in the abutment head above a bending zone. Key surfaces are above and below the break point. Solutions to ease adjustment of the inserted implant to the natural tooth position and which can reduce the danger of loosening of the inserted implant in the jawbone are coated on the implant.

25 Claims, 1 Drawing Sheet

SCREW IMPLANT APPARATUS AND METHOD

CROSS-REFERENCE TO RELATED APPLICATIONS

This application claims priority to international application German 20 2006 006 920.8 filed on Apr. 25, 2006.

BACKGROUND OF THE INVENTION

1. Field of the Invention

The present invention is in the field of bone implants, particularly dental implants.

2. Related Art

In spite of the greatest care in insertion of the base part of an implant into the jawbone, it is impossible to avoid subsequent adjustments as part of the prosthetic final servicing to achieve the required correct tooth position. To the extent that the implant superstructural part that will be inserted into the base part does not already have design features that allow subsequent correction or adjustment to the correct tooth position—DE 41 27 839 A1, screw implants, especially those made in a single piece—EP 1 468 658 A1, DE 203 06 008 U1, DE 39 18 309 C2—but also multi-part enossal implants—U.S. Pat. No. 4,645,435—have bendable sections or bending zones which make the required adjustments easier. These bendable sections are provided in the head region of the implant, below a cementation post or an abutment, and are formed by constrictions with a reduced profile cross-section.

The bendable segments designed in that manner provide, in an advantageous manner, for alignment of the implant head with the cementation post or the abutment with respect to the part of the implant inserted into the jawbone. But they also have the disadvantage that even with extreme care there is a high risk of breakage during the bending that must be done, because of the reduced profile cross-section in the neck region.

However, there is also a high risk of breakage in the final phase of the insertion, if the implant is already positioned relatively deeply within the jawbone but has not yet attained its final position, and a higher torque must be applied for further screwing the screw implant into the jawbone to attain its final position. This high risk of breakage occurs primarily if the implant bed has not been sufficiently prepared. After a break in the bendable neck region, it is extremely difficult and expensive to remove the broken implant, which has been inserted relatively solidly and deeply. But the broken implant must be removed so that the implant bed can be prepared again and a new or different implant can be inserted.

Maintaining the stability of enossal implants with respect to the bones into which they are placed is another problem. Mobility of implants is often observed both in orthopedic surgery and in dental and maxillofacial implantology. A certain portion of that mobility is due to infection. However, most of the mobility is caused by overloading the peri-implant bone. For instance, it is the most highly stressed screws, or the screws positioned in the least mineralized regions, such as in the tension or flexion regions of the bone, that become mobile in the case of fractured osteotomy plates.

The measures that have been known to limit or prevent these undesired processes amount to promoting new bone formation in the bony surgical region. Thus it has been suggested, among other things, to accelerate and stimulate the formation of new bony tissue by coating the implant surface with substances that promote bone growth.

Such procedures, and recommendations are, for instance, known from DE 600 19 752 T2, DE 196 30 034 A1 and DE 196 28 464 A1. They relate predominantly to improved preparation of substrates for bone development, such as tricalcium phosphate, hydroxyapatite, and all sorts of calcium and phosphorus compounds.

Measures for improved blood supply to the bone were also recommended to accelerate and stimulate formation of new bone tissue. Finally, increased provision of growth hormones and peptides of all types, which accelerate bone development, have been recommended.

None of those efforts has yet resulted in an actual useful and good clinical result, and there has been no overwhelming success in clinical practice, as it takes many weeks to months before the newly formed bone truly mineralizes and becomes capable of bearing a load. The implant mobility mentioned occurs much sooner, though.

Therefore the invention is based on the objective of reducing the disadvantages connected with breakage of the screw implant in the head and neck region with simultaneous improvement of the bendability in the neck region of the implant, and, by means of a suitable coating, to produce a microtherapeutic reduction of the osteonal activity, so as to prevent in that manner destabilization of the inserted implant.

The present invention concerns a further-improved enossal screw implant that is inserted cortically into the jawbone as an implant base, and which has at its head end a neck region with a bending zone, to which an abutment connects for holding and fastening the superstructural part of a tooth replacement or a substructure.

SUMMARY OF THE INVENTION

In contrast to the solutions previously known, the screw implant according to the invention that is designed in one piece and preferably provided with an abutment has a break point in the vicinity of the abutment head, so that the diameter of the profile cross-section at this break point is slightly less than the minimum diameter in the vicinity of the bendable neck section with reduced profile cross-section, which has preferably an elliptical or bar-shaped profile. The longitudinal axis of the selected profile forms the preferred, established bending line and is indicated in an advantageous manner by a mark on the head surface of the implant.

If, for various reasons, high torques occur that could result in breakage of the implant in the vicinity of the bendable neck section when the implant is being inserted into the prepared implant bed, then because of the design according to the invention the break does not occur in the vicinity of the bendable neck section, with the resulting disadvantages, but at the break point, which has a profile cross section smaller than that in the vicinity of the bendable neck section.

In order to remove an implant that has broken in the vicinity of the break point during insertion of the implant into the prepared implant bed, and which is already screwed relatively firmly into the jaw bone, simply and with a minimum of additional cost, other key surfaces are provided below the break point to accept a suitable tool for unscrewing the broken implant. It is convenient for the key surfaces which extend from the head surface of the abutment in the direction of the implant foot to be carried on so that they end between the break point and the bendable neck section of the implant.

The bendable neck section preferably has a bending zone with a previously established preferred bending line which is indicated by a mark on the head surface of the abutment or of the cementation post and which is determined by the profile cross-section in the bending zone. The profile cross-section is preferably of elliptical or bar shape, with which the longitudinal axis of the selected profile forms the preferred established bending line.

In this way, the relevant profile cross-section in the neck section is increased for the bending measures that must be applied to adjust the tooth position, so that the danger of breakage is further reduced. At the same time the accurate positioning of the implant on insertion is simplified by the indication of the preferred, established bending line on the head surface of the implant, and shows quite visibly, even after healing in, the direction in which the implant head with the abutment or a cementation post can preferably be bent to make the necessary adjustments for an exact tooth position.

In contrast to the previously known solutions which, without exception, use substances that accelerate and stimulate formation of new bone tissue to stabilize enossal implants, the solution according to the invention takes a fundamentally different route, using substances to coat the implant that temporarily and locally limited, inhibit or prevent the internal new formation of bone, called remodeling.

Such substances are used, for instance, to treat osteoporosis if there is a need to delay bone deterioration caused by remodeling. These substances affect the activity of the so-called osteoclasts. They reduce the activity, propagation, or motility of the osteoclasts, the cells that degrade bone. At the state of the art, those substances are administered orally or parenterally for general medical problems (such as osteoporosis).

These substances have substantial adverse effects in the area of implantology, though, if they are administered in that manner. For instance, very severe inflammations can occur after implantation, as in patients who have received enossal dental implants or surgical-orthopedic implants. The most feared complications are the notorious osteomyelitis (inflammation of the bone marrow) and osteonecrosis (death of bones without bacterial action). For those reasons, implantations in patients who are taking such substances for general medical reasons are now considered highly risky and essentially contraindicated. The reason is quite simple: Because of the reduced activity of the osteoclasts, the bone is less ossified. As a result, it is more strongly mineralized and the blood supply that is important for defense is lacking. Now if such a damaged bone is exposed to surgery, unintended penetration of bacteria into the bony surgical field can occur. Then, because the blood supply is inadequate, those bacteria cannot be repelled by the body's immune system, and they can propagate.

Even entire regions of bone can die in the same manner under therapy with substances that prevent or hinder osteonal remodeling. It is often not realized that the bone is dead, because dead bone retains its structural integrity for a long time, and even when dead, can transfer force and appear as a morphologic structure.

On the other hand, overloaded bone with microdefects due to the use of substances that inhibit or prevent osteonal remodeling, plus the repair damages that are harmful with respect to structural integrity, breaks after only about six weeks.

Controlled histological studies on which the invention is based show that the severe side effects of the substances that prevent the osteonal system from developing and functioning can be avoided for the region of the implant by not administering those substances orally or parenterally, but locally as part of the actual surgery, microtherapeutically in a sense. Coating of the implant with the active substance is an advantageous form of application. As many implant surfaces have a certain roughness in any case, application of such a coating is not a problem.

It has also been found that both fat-soluble and water-soluble substances can be used equally well. Thus, a great range of substances can be used for the solution according to the invention: beyond the biphosphonates—namely etidronate, clodronate, tiludronate, pamidronate, alendronate, risedronate, ibandronate, zoledronate and combinations thereof—estrogens, TGF-beta, gallium nitrate, Plicamycin, Calcitriol, Calcetonin, Bafilomycin and combinations thereof are also materials suitable for implant coating according to the invention.

In searching for substances that can be used in the implant region to reduce osteonal activity in the vicinity of implants, but which are not toxic, it was found that even a thin coating with pure sodium chloride has such a local inhibitory action on the osteoclastic activity involved in remodeling. Such a coating can be produced by immersing the implant (with a roughened surface of those parts integrated into the jawbone by way of osseointegration, if possible) in a sodium chloride solution (such as min. 0.9% sodium chloride) at the end of the cleaning procedure and then drying it carefully. Thus, a thin coating of pure sodium chloride remains on the surface. This layer dissolves in the fluid and in the local blood during and after insertion of the implant. That produces a site of higher salt concentration in the bone, which limits the implant. Histological examinations have shown that this concentration influences the remodeling. It is not sufficient for just the usual physiological solution of sodium chloride to be present. The concentrations in the surrounding bone must be far higher than those that occur physiologically in the blood.

The same is true for a thin, soluble coating with CaP, $CaSO_4$, and other bone substrate substances that exhibit an action similar to that of sodium chloride. It is the massive local elevation of the concentration of these substances and the rapid solubility of the substances that is critical. They cannot adhere firmly to the implant surface (as, for instance, the older CaP coating intended to be permanent, or earlier hydroxyapatite coatings) but must be able to diffuse easily into the adjoining osteonal systems.

Colloidally applied pure silver also exhibits particularly favorable properties, especially at a particle size of 0.0001-0.01 μm. It is already known that this substance inhibits bacterial colonization. It has been found, though, that cells appearing in osteonal systems are also inhibited by silver. Concentrations between 10 ppm and 1500 ppm exhibit particularly favorable effects in this connection.

So if a high ion or particle concentration is generated around the implant by means of the substances mentioned above, remodeling can be prevented for a certain period, namely until the implants become splinted orthopedically (by the prosthesis). If one selects non-toxic, degradable substances to achieve the effect as per the invention, they can easily be degraded later, so that the long-term osteopetrotic effect ceases and the peri-implant bones regenerate normally with time. For example, colloidal silver can be attacked in the osteonal remodeling that occurs later and can be moved away in a subperiostal or endosteal direction, where it is eventually absorbed and then eliminated enterally without problems.

As a result of the coating according to the invention, there is a situation near the enossal implant surface in which the bone exhibits no spatially limited and almost no temporally limited repair signs. Thus, the implants also remain stable postoperatively.

The concentration of the substances used for the coating according to the invention decreases with time, due to simple diffusion. They are diluted by the liquid circulating in the bones and by the blood flow, so that their concentration decreases below the threshold of therapeutic activity and regular remodeling slowly becomes possible again. By that time, though, the implants are finally well integrated into the bone and damages from use (microcracks) which act on the bones can no longer accumulate with time with repair defects. The repair also proceeds more slowly.

It can be advantageous, likewise, to be able to combat any local infections or to prevent such infections prophylactically, to combine the previously named substances for coating with an antibiotic. Individual substances suggested according to the invention are themselves antibiotically active, e.g., calcium sulfate, calcium phosphate, and silver. Thus it may be sufficient also to combine several of the substances named for the coating.

A further advantageous substance comprises the combination of a bisphosphonate, such as ibandronate, with an antibiotic, such as treacycline. The use of bafilomycin alone, on the other hand, can develop both effects. In appropriate concentration, it acts as an antibiotic and also as an inhibitor of osteonal remodeling.

According to a further feature of the invention, a foot section connects to the neck region in the direction of the implant foot. It comprises, optionally, a cylindrical with a subsequent conical foot section, or, in a manner which is itself known, it can be designed entirely conically. Both the cylindrical and the conical foot section have threads with which the implant is screwed into the implant bed in the jawbone.

To further promote solid and enduring seating of the implant in the jawbone, an additional terminal section is arranged on the implant according to the invention, which connects to the conical food section and which preferably has a profiled jacket surface, for instance, in the form of a sawtooth profile. For certain applications, for instance, if sufficient bone substance is present, the terminal section can be separated from the remainder of the implant body in a simple way at the break point, through which the terminal section is connected to the conical food section.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

Figure 1:
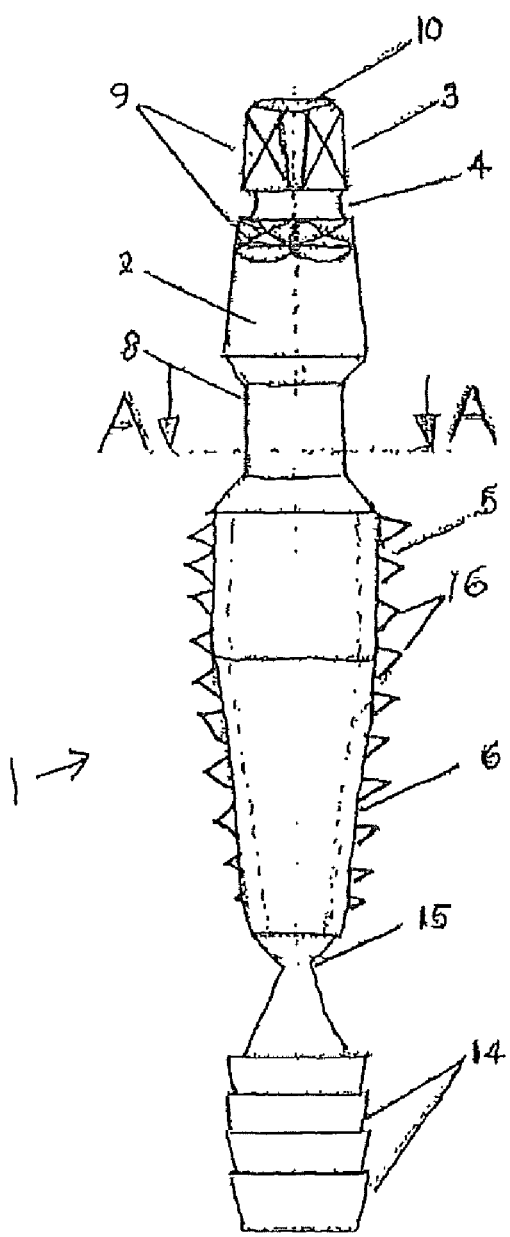
FIG. 1 is an overall view of the screw implant according to the invention.
Figure 2:
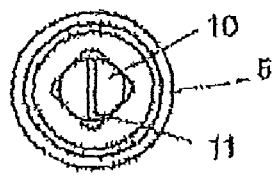
FIG. 2 is a plan view on the head surface of the implant.
Figure 3:
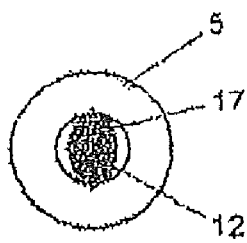
FIG. 3 is an advantageous profile cross-section in the neck region with an established bending line.
Figure 4:
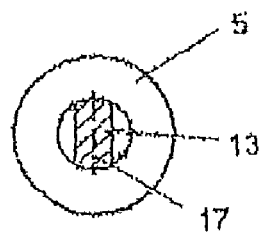
FIG. 4 is an advantageous profile cross-section in the neck region with an established bending line.

DEPICTED COMPONENTS INCLUDE (1) Screw implant;
(2) Abutment;
(3) Abutment head;
(4) Predetermined breaking point;
(5) Cylindrical foot section;
(6) Conical foot section;
(7) Terminal section;
(8) Neck section;
(9) Wrench flats;
(10) Head surface;
(11) Mark;
(12) Profile cross-section in the bending zone;
(13) Bar;
(14) Sawtooth profile;
(15) Second predetermined breaking point;
(16) Thread; and
(17) Bending line.

DETAILED DESCRIPTION OF THE PREFERRED EMBODIMENTS

The following description of the preferred embodiment(s) is merely exemplary in nature and is in no way intended to limit the invention, its application, or uses.

The screw implant 1 according to the invention is preferably provided with an abutment 2, and has a break point 4 with a reduced profile cross-section in the vicinity of the abutment head 3. The profile cross-section of this break point 4 is chosen so that any break that can be caused, for example, by occurrence of elevated torque on inserting the screw implant 1 occurs at this break point 4, before a break occurs in the vicinity of the bendable neck section 8 with a reduced profile cross section.

The break point 4 is preferably in the vicinity of the key surfaces 9 which accept a suitable tool for screwing in the screw implant 1. The break point 4 is arranged so that the key surfaces 9 extending from the head area 10 of the abutment head continue below the break point 4 and end between the bendable neck section 8 and the break point 4.

In case of a break, the insertion tool can be placed on the remaining key surfaces 9 below the break point 4 and the broken screw implant 1 can be unscrewed out of the implant bed in a relatively simple way.

The reduced profile cross-section of the bendable neck section 8 forms a bending zone with a previously established bending line, which is marked on the head surface of the implant and is determined by the selected profile in the bending zone. According to the present invention, the bending zone has an elliptical profile or the form of a bar 13, which can, for example, be produced by milling. The longitudinal axes of this profile form the bending lines 10; 11, which are indicated by the mark 9 in the head surface 8, indicating the preferred direction of bending for subsequent bending operations, in which the danger of breakage of the profile cross-section in the bending zone is a minimum because of the design of the profile cross-section according to the invention.

The implant base that is to be held by the jawbone is formed of a foot section which consists of a cylindrical foot segment 5 and a conical foot segment 6. As a deviant from the design shown, the foot section can also be made up of an over-all conical foot section 6. Both the cylindrical and the conical foot sections are provided with a thread 16 for screwing the implant 1 into the jawbone.

The implant base ends at an end section 7, which connects to the conical foot section through a breakpoint 15 and which can, if necessary, be separated from the remaining body of implant 1 at breakpoint 15.

The enossal surface of the implant is preferably provided with a microporous surface structure by known processes, and after cleaning of the implant, an adherent water-soluble or fat-soluble ibandronate solution is also applied, so that the active substance occurs at a dosage of 3 to 8 mg in the coating on the enossal surface of the implant.

In the absence of the microporous surface structure, the adherent water-soluble or fat-soluble ibandronate solution of the stated dosage can also be applied directly onto the enossal surface of the implant. This coating is preferably applied to the enossal surface immediately before insertion of the implant, and the implant is inserted into the prepared cavity after the applied coating has dried.

The screw implant may have a foot section comprised of a threaded portion and a saw tooth portion. As depicted, the threads 16 cover the cylindrical foot segment and the conical foot segment 6. The saw tooth profile 14 covers the terminal section 7.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A bone implant comprising:
    a foot section;
    a neck section, said neck section being connected to said foot section, and said neck section having a bending zone;
    an abutment head connected to the neck section in a one-piece form to mount a tooth replacement thereon;
    said abutment head having a break point;
    said abutment head being dimensioned to provide supporting fixation surfaces for attachment of a tooth replacement, said surfaces including at least one key surface such that a torque may be applied to said abutment head for installing said implant; and
    a diameter of a profile cross-section at said break point being less than a minimum thickness of said bending zone of said neck section, such that said break point breaks at a lower torque than a torque that would break said implant at said bending zone;
    whereby any unintended break occurring during installation will be at said break point.

2. The bone implant according to claim 1, wherein said key surface is provided below the break point.

3. The bone implant according to claim 2, wherein said key surface ends between the break point and the neck section.

4. The bone implant according to claim 1, wherein the bending zone has an elliptical, oval-shaped profile cross-section with a predetermined bending line, with the minimum diameter in the profile cross-section being smaller than a largest diameter of a thread.

5. The bone implant according to claim 1, wherein an orientation of the bending zone is indicated by a mark on a head surface of the bone implant.

6. The bone implant according to claim 1 wherein said foot section consisting of a cylindrical foot section and a conical foot section connected, said cylindrical foot section being connected to the bending zone.

7. The bone implant according to claim 6 wherein at least one of the cylindrical foot section or the conical foot section are provided with a thread.

8. The bone implant according to claim 1 wherein a terminal section is separably connected with the foot section through a second break point.

9. The bone implant according to claim 1 wherein said foot section has a threaded portion and a saw tooth portion.

10. The bone implant according to claim 1 wherein the foot section is a conical foot section.

11. The bone implant according to claim 1 wherein the profile cross-section at the bending zone is selected from the group consisting of a bar and an elliptical shape and the longitudinal axis of the ellipse is a predetermined bending line.

12. The bone implant according to claim 1 further comprising: a coating, said coating including an active substance that delays osteonal remodeling of the jaw bone in the vicinity of an implantation osteotomy, is applied onto enossal surfaces of the bone implant.

13. The implant according to claim 12, wherein the active substance in the coating is a bisphosphonate.

14. The implant of claim 12 wherein the coating contains an adherent water-soluble or fat soluble ibandronate solution.

15. The implant of claim 14 wherein said ibandronate is selected from the group consisting of an etidronate, a clodronate, a tiludronate, a pamidronate, an alendronate, a risedronate, an ibandronate, a zoledronate or a combination of them as the active substance.

16. The implant according to claim 12 wherein the active substance in the coating is selected from the group of estrogens.

17. The implant of claim 12 wherein the coating contains TGF-beta, gallium nitrate, plicamycin, calcitriol, calcetonin, bafilomycin or combinations of them as the active substance.

18. The implant according to claim 12 wherein the active substance in the coating is selected from the group consisting of structural substances occurring in the bone or salts of the bone.

19. The implant according to claim 12 wherein the active substance in the coating is present at a concentration that is above the normal physiological blood concentration of that substance.

20. The implant according to claim 12 wherein the coating comprises sodium chloride.

21. The implant according to claim 12 wherein the coating contains a calcium compound.

22. The implant according to claim 12 wherein the coating contains calcium phosphate or calcium sulfate.

23. The implant according to claim 12 wherein the active substances of the coating is combined with substances having antibiotic activity.

24. The implant according to one of claim 12 wherein the coating contains an antibiotic at a concentration selected to inhibit osteonal remodeling.

25. The implant according to claim 12 wherein the coating contains silver in an approximately pure form and said silver has a particle size of 0.0001-0.01 micron.

* * * * *